(12) United States Patent
Salehi et al.

(10) Patent No.: US 8,986,285 B2
(45) Date of Patent: Mar. 24, 2015

(54) SELF-CLEANING SURGICAL SUCTION DEVICE

(75) Inventors: Sean A. Salehi, Chicago, IL (US); Jeffrey N. Wickham, Geyserville, CA (US)

(73) Assignee: Neuro Enterprises, LLC, Chicago, IL (US)

( * ) Notice: Subject to any disclaimer, the term of this patent is extended or adjusted under 35 U.S.C. 154(b) by 569 days.

(21) Appl. No.: 13/420,542

(22) Filed: Mar. 14, 2012

(65) Prior Publication Data

US 2012/0289941 A1    Nov. 15, 2012

Related U.S. Application Data

(60) Provisional application No. 61/464,922, filed on Mar. 14, 2011.

(51) Int. Cl.
| A61M 1/00 | (2006.01) |
| A61C 17/06 | (2006.01) |
| A61B 19/00 | (2006.01) |

(52) U.S. Cl.
CPC .............. *A61M 1/008* (2013.01); *A61B 19/34* (2013.01); *A61C 17/043* (2013.01); *A61M 1/0047* (2013.01)
USPC ...................................................... 604/540

(58) Field of Classification Search
CPC ........ A61B 10/00; A61B 10/02; A61B 17/34; A61B 17/3415; A61B 17/3417; A61M 1/00; A61M 5/24; A61M 5/31; A61M 25/00; A61M 25/09; A61M 39/00
USPC ................. 604/93.01, 156, 158, 161, 164.01, 604/164.02, 162.04, 164.07, 164.11, 604/165.02, 181, 187; 600/562, 566, 567, 600/573

See application file for complete search history.

(56) References Cited

U.S. PATENT DOCUMENTS

| 3,375,828 | A | * | 4/1968 | Sheridan | ....................... 604/119 |
| 4,022,218 | A |   | 5/1977 | Riddick |   |
| 4,699,138 | A |   | 10/1987 | Behrstock |   |
| 4,886,492 | A |   | 12/1989 | Brooke |   |
| 5,195,952 | A |   | 3/1993 | Solnit |   |
| 5,320,110 | A | * | 6/1994 | Wang | ............................ 600/566 |

(Continued)

OTHER PUBLICATIONS

PCT International Search Report: PCT application PCT/US2012/029131 filed on Mar. 12, 2012 and published as WO 2012-125769 on Sep. 20, 2012.

(Continued)

*Primary Examiner* — Melanie Hand
(74) *Attorney, Agent, or Firm* — David G. Rosenbaum; J. Peter Paredes; Rosenbaum IP, P.C.

(57) ABSTRACT

A suction device is disclosed that includes a suction tube having a first longitudinal axis, and proximal and distal openings; a guide tube that is substantially coextensive with and parallel to the suction tube, and has a second longitudinal axis, and proximal and distal openings; a stylet having proximal and distal ends; and a junction conduit having proximal and distal openings; wherein the stylet is disposed along the second longitudinal axis and encircled by the guide tube, and the proximal opening of the junction conduit contacts the distal opening of the suction tube and the distal opening of the guide tube such that the distal opening of the junction conduit is in fluid communication with the suction tube, and urging the stylet through the guide tube translates the stylet to the distal opening of the junction conduit.

6 Claims, 11 Drawing Sheets

(56) References Cited

U.S. PATENT DOCUMENTS

| | | |
|---|---|---|
| 5,591,141 A | 1/1997 | Nettekoven |
| 5,643,229 A | 7/1997 | Sinaiko |
| 5,779,649 A | 7/1998 | Herbert |
| 6,045,516 A | 4/2000 | Phelan |
| 6,146,136 A | 11/2000 | Tenniswood |
| 6,881,060 B2 | 4/2005 | Lundgren |
| 6,908,455 B2 | 6/2005 | Hajianpour |
| D571,458 S | 6/2008 | Kataoka |
| 2007/0219499 A1 | 9/2007 | Hayakawa et al. |

OTHER PUBLICATIONS

PCT International Preliminary Report on Patentability (Chapter I): PCT application PCT/US2012/029131 filed on Mar. 12, 2012 and published as WO 2012-125769 on Sep. 20, 2012.

\* cited by examiner

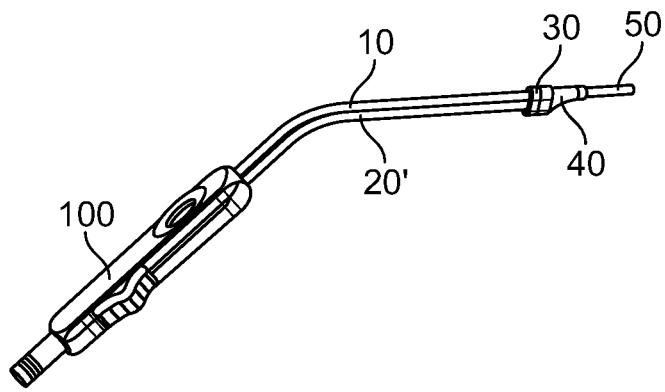
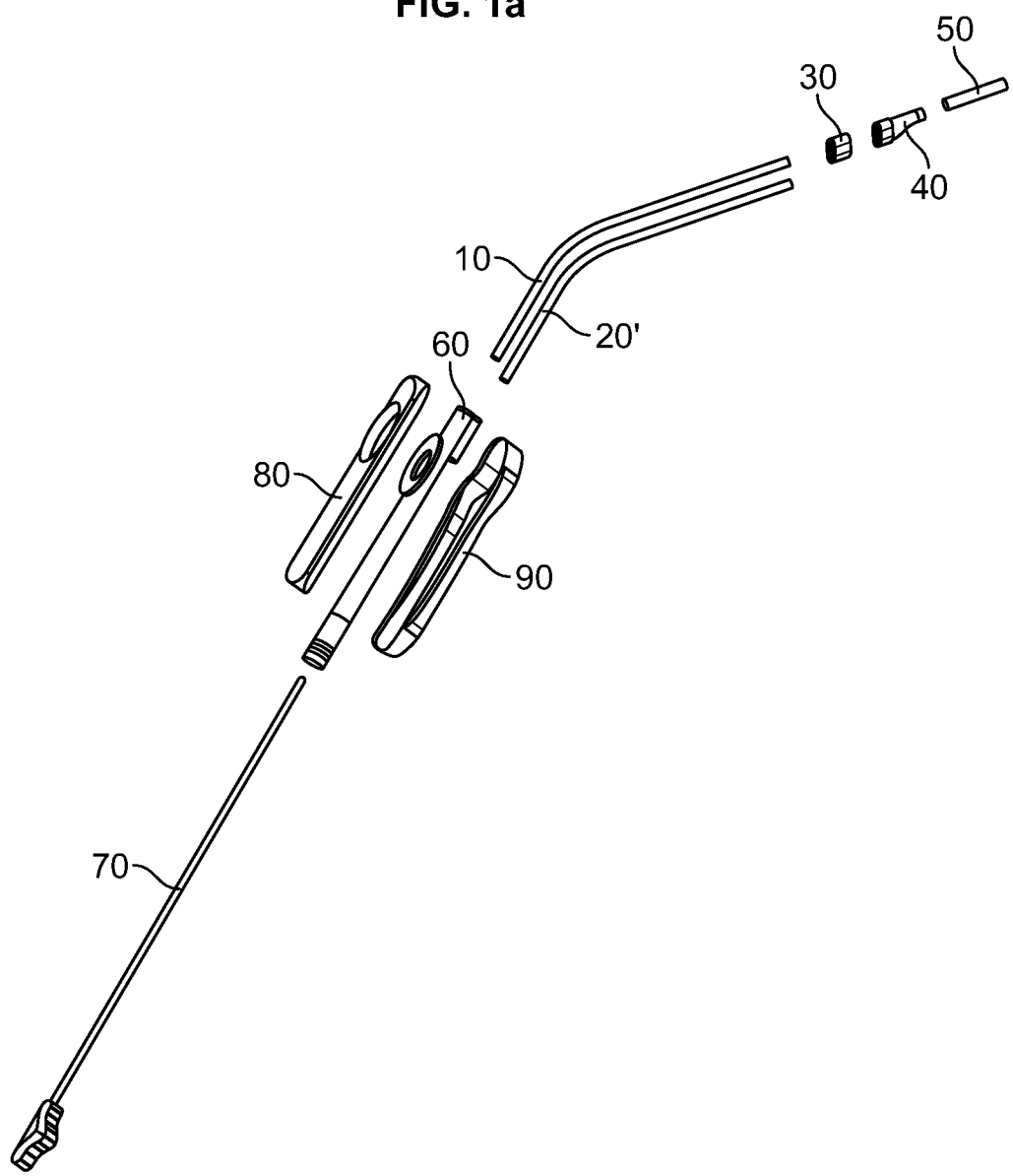
FIG. 1a
FIG. 1b

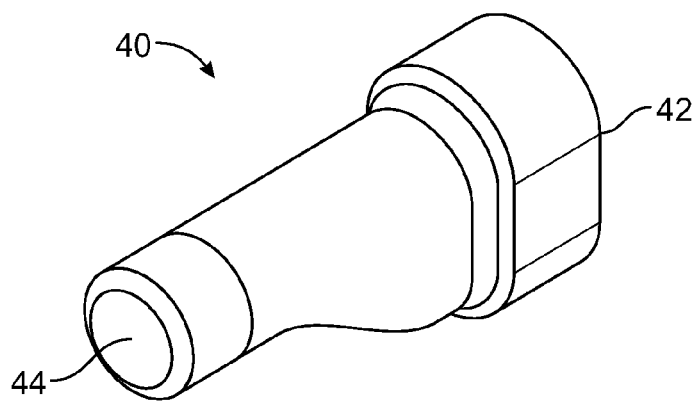
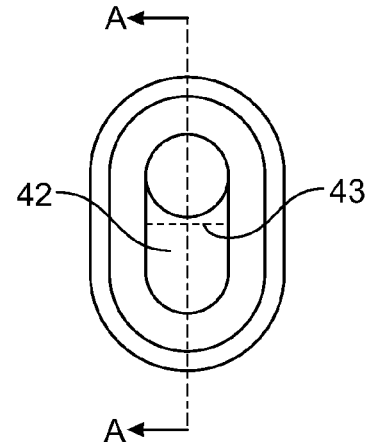
FIG. 5a
FIG. 5b
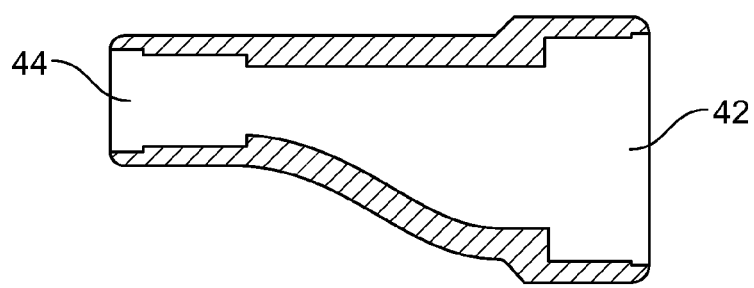
FIG. 5c
FIG. 6

SECTION A-A

SELF-CLEANING SURGICAL SUCTION DEVICE

CROSS-REFERENCES TO RELATED APPLICATIONS

This application claims priority to U.S. Provisional Application Ser. No. 61/464,922, filed Mar. 14, 2011, herein incorporated by reference in its entirety.

FIELD OF THE INVENTION

The present invention relates to the field of surgical instruments employed for removing debris from within a surgical operative field. In particular, the present invention is a tubular suction device for surgical, dental, or veterinary use that includes a means for self-clearing debris from its intake portion.

BACKGROUND

A common requirement for any surgical procedure on a patient is that the operative field opened in the patient must be continually cleared of fluids and particulates that obscure the surgeon's vision of the field. These fluids and particulates can include blood, irrigating solution, bone chips or dust, hemostatic agents, among others. Irrespective of the region of the body where the surgery occurs, but especially with respect to neurological or orthopedic procedures, significant amounts of these fluids and particulates present challenges to the surgeon's clear viewing of the surgical field. In addition to the fluids and particulates derived from the patient, foreign materials usefully employed as hemostatic agents can also obscure the operative field and require removal. Such hemostatic agents include absorbable gelatin sponges (e.g., Gelfoam from Baxter Healthcare Corporation), a kneadable mixture of beeswax and mineral wax (e.g., Ethicon Bone Wax from Johnson & Johnson), or an oxidized cellulose polymer (e.g., a polymer of polyanhydroglucuronic acid sold under the trade name Surgicel by Johnson & Johnson).

Removing these materials is typically accomplished using a surgical suction device, inserting the distal tip of the surgical suction device in and about the operative field whereupon the field-obscuring materials are sucked away to a location outside of the field; until, that is, the distal tip becomes fouled by particulate matter or coagulated blood or combinations of such, which is inevitable.

The distal tip is commonly referred to as a surgical suction tip and is an integral part of any surgical procedure. More particularly to the general view of the problem presented above, the suction tip is connected to a wall suction unit in the surgical suite via a plastic tubing. The suction (referred to below as negative pressure) created at the tip clears the field of the materials mentioned above that may be obstructing the surgeon's field of view.

The practical approach taken in a surgery to clear the clogged suction tips is to interrupt the surgery so the tip can be cleaned. Literally, the surgeon stops clearing the operative field, hands the clogged suction to the scrub nurse so s/he can clear it with saline flushes or a stylet (i.e., an implement employed to poke at and remove obstructing matter from a vacuum path). This process may have to be repeated multiple times in a surgery, prolonging the surgical time and contributing a significant source of inefficiency to the surgical procedure.

Despite the development of various shapes of the suction tip inspired by the desire to eliminate the clogged distal tip problem, clogging of the suction tip remains a problem in all operating rooms. Accordingly, the surgeon uses the surgical suction device until its distal tip becomes clogged, hands it to an assistant who, under sterile conditions, manually replaces or unclogs the tip and hands the surgical suction device back to the surgeon. Obviously, critical time is lost by the need to hand the surgical suction device to an assistant for clearance, and then get it back, and then place it where it can do its intended task until, alas, the cycle is repeated with the distal tip yet again clogged, lost time, and a patient in surgery longer than necessary.

It would be desirable to have a surgical suction device designed that allowed the surgeon to clear the distal tip directly without need to pass it off to another or otherwise lose time completing the work of addressing the patient's issues that caused the opening of the operative field in the first place.

SUMMARY

To address these problems arising from frequently clogged surgical suction devices, the invention claimed herein enables the surgeon alone to remove obstructions at the distal tip of the surgical suction device. This invention thus bypasses the need for an assistant who, under sterile conditions, is handed a clogged surgical suction device, then manually replaces or unclogs the tip, and hands the surgical suction device back to the surgeon. The invention described herein also functions seamlessly with suction tips of various shapes, thus providing a surgeon with a choice of tip shapes suitable to the application.

In a first embodiment, the invention described herein includes: (a) a suction tube having a first longitudinal axis, a proximal opening, and a distal opening; (b) a guide structure having a second longitudinal axis that is substantially parallel to the first longitudinal axis, a proximal opening, and a distal opening; (c) a stylet having a proximal end and a distal end; and (d) a junction conduit having a proximal opening and a distal opening; wherein, the stylet is disposed along the second longitudinal axis and encircled by the guide structure, and the proximal opening of the junction conduit is in contact with at least the distal opening of the suction tube such that the distal opening of the junction conduit is in fluid communication with the suction tube. Urging the stylet through the guide structure along the second longitudinal axis through the junction conduit translates the distal end of the stylet to the distal opening of the junction conduit.

In a second embodiment, the invention further includes a knob that is fixed at or about the proximal end of the stylet; and/or a tubular base member having a proximal vacuum connector, an intermediate region, and a distal attachment region that are each in fluid communication with one another, wherein the distal attachment region is in contact with the proximal opening of the suction tube such that the proximal vacuum connector is in fluid communication with the suction tube. The tubular base member can include a vent feature disposed on the intermediate region of the tubular base member that is in fluid communication with a vacuum source connected to the vacuum connector at the proximal end of the tubular base member. The vent can control the negative pressure exhibited at the site of the surgical field by the degree to which it is obstructed. To facilitate the degree of obstruction to the vent, the tubular base member includes a vent-surrounding member disposed on the intermediate region. The vent also acts as a muffler to reduce sound created by the flow of air.

In a third embodiment, a receiving member disposed at the distal attachment region encircles the stylet and is coaxial with the guide structure along the second longitudinal axis.

A fourth embodiment includes a handle member that is operably attached to and surrounds the intermediate region and distal attachment region and includes a track element extending substantially parallel to the second longitudinal axis that is proximate to the distal attachment region. A vent-access opening can also be included and disposed such that the vent and vent-surrounding member are accessible through the vent-access opening.

A fifth embodiment includes a tubular tip that contacts and is in fluid communication with the junction conduit.

For convenience of use, in some embodiments the suction tube is bent between the proximal end and distal end. When the suction tube is employed in a bent configuration, the guide structure may also be bent between the proximal end and distal end.

To stabilize the position of the guide structure, the receiving member is in contact with the proximal opening of the guide structure, and a bracket may be disposed proximate to the distal end of the suction tube and proximate to the distal end of the guide structure to conjoin the suction tube and guide structure.

The invention may have a guide structure that is a guide tube that is substantially parallel to and coextensive with the suction tube.

In some cases the guide structure is a shortened guide tube that is substantially parallel to the suction tube, and yet in other cases the guide structure is at least one annulus disposed on the suction tube.

In a sixth embodiment the suction device includes: (a) a suction tube having a first longitudinal axis, a proximal opening, a distal opening, and an entry port disposed proximate to the distal opening; (b) a guide structure having a second longitudinal axis that is substantially parallel to the first longitudinal axis, a proximal opening, and a distal opening; and (c) a hooked stylet having a proximal end and a hooked distal end; wherein, the stylet is disposed substantially along the second longitudinal axis and encircled by the guide structure such that the hooked distal end is disposed in or proximate to the entry port. As the hooked stylet is urged in the distal direction substantially along the second longitudinal axis and through the guide structure, the curvature of the hooked distal end meeting resistance from the distal edge of the entry port translates the hooked stylet into the suction tube and to the distal opening of the suction tube.

In a seventh embodiment, the invention further includes a knob that is fixed at or about the proximal end of the stylet; and/or a tubular base member having a proximal vacuum connector, an intermediate region, and a distal attachment region that are each in fluid communication with one another, wherein the distal attachment region is in contact with the proximal opening of the suction tube such that the proximal vacuum connector is in fluid communication with the suction tube. The tubular base member can include a vent feature disposed on the intermediate region of the tubular base member that is in fluid communication with a vacuum source connected to the vacuum connector at the proximal end of the tubular base member. The vent can control the negative pressure exhibited at the site of the surgical field by the degree to which it is obstructed. To facilitate the degree of obstruction to the vent, the tubular base member includes a vent-surrounding member disposed on the intermediate region. The vent also acts as a muffler to reduce sound created by the flow of air.

In an eighth embodiment, a receiving member disposed at the distal attachment region encircles the stylet and is coaxial with the guide structure along the second longitudinal axis.

A ninth embodiment includes a handle member that is operably attached to and surrounds the intermediate region and distal attachment region and includes a track element extending substantially parallel to the second longitudinal axis that is proximate to the distal attachment region. A vent-access opening can also be included and disposed such that the vent and vent-surrounding member are accessible through the vent-access opening.

For convenience of use, in some embodiments the suction tube is bent between the proximal end and distal end. When the suction tube is employed in a bent configuration, the guide structure may also be bent between the proximal end and distal end.

To stabilize the position of the guide structure, the receiving member is in contact with the proximal opening of the guide structure, and a bracket may be disposed proximate to the distal end of the suction tube and proximate to the distal end of the guide structure to conjoin the suction tube and guide structure.

The invention may have a guide structure that is a shortened guide tube that is substantially parallel to the suction tube, and yet in other cases the guide structure is at least one annulus disposed on the suction tube.

A tenth embodiment of the suction device includes: (a) a suction tube having a first longitudinal axis, a proximal opening, a distal opening, and an entry port disposed proximate to the distal opening; (b) a guide structure having a second longitudinal axis, a proximal opening, and a distal opening; and (c) a stylet having a proximal end and a distal end; wherein, the stylet is disposed substantially along the second longitudinal axis and encircled by the guide structure, and the distal opening of the guide structure is in contact with the entry port of the suction tube and in fluid communication with the distal opening. Urging the stylet through the guide structure substantially along the second longitudinal axis translates the distal end of the stylet through the entry port of the suction tube to the distal opening of the suction tube.

In an eleventh embodiment, the invention further includes a knob that is fixed at or about the proximal end of the stylet; and/or a tubular base member having a proximal vacuum connector, an intermediate region, and a distal attachment region that are each in fluid communication with one another, wherein the distal attachment region is in contact with the proximal opening of the suction tube such that the proximal vacuum connector is in fluid communication with the suction tube. The tubular base member can include a vent feature disposed on the intermediate region of the tubular base member that is in fluid communication with a vacuum source connected to the vacuum connector at the proximal end of the tubular base member. The vent can control the negative pressure exhibited at the site of the surgical field by the degree to which it is obstructed. To facilitate the degree of obstruction to the vent, the tubular base member includes a vent-surrounding member disposed on the intermediate region. The vent also acts as a muffler to reduce sound created by the flow of air.

In a twelfth embodiment, a receiving member disposed at the distal attachment region encircles the stylet and is coaxial with the guide structure along the second longitudinal axis.

A thirteenth embodiment includes a handle member that is operably attached to and surrounds the intermediate region and distal attachment region and includes a track element extending substantially parallel to the second longitudinal axis that is proximate to the distal attachment region. A vent-access opening can also be included and disposed such that the vent and vent-surrounding member are accessible through the vent-access opening.

In a fourteenth embodiment, the guide structure is an alternative guide tube wherein the suction tube and alternative guide tube are bent between their respective proximal and distal ends such that the suction tube and guide structure are substantially parallel until the distal opening of the alternative guide tube connects with the entry port on the suction tube.

In a fifteenth embodiment, the suction device includes: (a) a suction tube having a first longitudinal axis, a proximal opening, a distal opening, and an entry port disposed proximate to the distal opening; (b) a guide structure having a second longitudinal axis that is substantially parallel to the first longitudinal axis, a proximal opening, and a distal opening; (c) a stylet having a proximal end and a distal end; and (d) a lip disposed about the distal end of the entry port; wherein, the stylet is disposed along the second longitudinal axis and encircled by the guide structure, and as the stylet is urged through the guide structure along the second longitudinal axis the distal end of the stylet moves along the curvature or slope of the lip and is translated through the entry port to the distal opening of the suction tube.

In a sixteenth embodiment, the invention further includes a knob that is fixed at or about the proximal end of the stylet; and/or a tubular base member having a proximal vacuum connector, an intermediate region, and a distal attachment region that are each in fluid communication with one another, wherein the distal attachment region is in contact with the proximal opening of the suction tube such that the proximal vacuum connector is in fluid communication with the suction tube. The tubular base member can include a vent feature disposed on the intermediate region of the tubular base member that is in fluid communication with a vacuum source connected to the vacuum connector at the proximal end of the tubular base member. The vent can control the negative pressure exhibited at the site of the surgical field by the degree to which it is obstructed. To facilitate the degree of obstruction to the vent, the tubular base member includes a vent-surrounding member disposed on the intermediate region. The vent also acts as a muffler to reduce sound created by the flow of air.

In a seventeenth embodiment, a receiving member disposed at the distal attachment region encircles the stylet and is coaxial with the guide structure along the second longitudinal axis.

An eighteenth embodiment includes a handle member that is operably attached to and surrounds the intermediate region and distal attachment region and includes a track element extending substantially parallel to the second longitudinal axis that is proximate to the distal attachment region. A vent-access opening can also be included and disposed such that the vent and vent-surrounding member are accessible through the vent-access opening.

For convenience of use, in some embodiments the suction tube is bent between the proximal end and distal end. When the suction tube is employed in a bent configuration, the guide structure may also be bent between the proximal end and distal end.

To stabilize the position of the guide structure, the receiving member is in contact with the proximal opening of the guide structure, and a bracket may be disposed proximate to the distal end of the suction tube and proximate to the distal end of the guide structure to conjoin the suction tube and guide structure.

The invention may have a guide structure that is a shortened guide tube that is substantially parallel to the suction tube, and yet in other cases the guide structure is at least one annulus disposed on the suction tube.

The foregoing and other features and advantages of the invention are apparent from the following detailed description of embodiments read in conjunction with the accompanying drawings. The detailed description and drawings are merely illustrative of the invention rather than limiting. The scope of the invention is defined by the appended claims and equivalents thereof. It is intended that all changes or modification within the meaning and range of equivalents are embraced by the claims.

BRIEF DESCRIPTION OF THE DRAWINGS

FIG. 1a is a perspective view of one embodiment of the self-cleaning surgical suction device.

FIG. 1b is a perspective blown up view of the embodiment of the self-cleaning surgical suction device depicted in FIG. 1a.

FIG. 2b is a frontal view from the distal end of the suction tube depicted in FIG. 2a.

FIG. 3b is a frontal view from the distal end of the guide tube depicted in FIG. 3a.

FIG. 5a is a perspective view of the junction element.

FIG. 5b is a frontal view of the proximal opening of the junction conduit.

FIG. 5c is a cross sectional view of the junction conduit along section A-A.

FIG. 6 is a profile view and frontal view of the tubular tip.

DETAILED DESCRIPTION

Figure 2A:
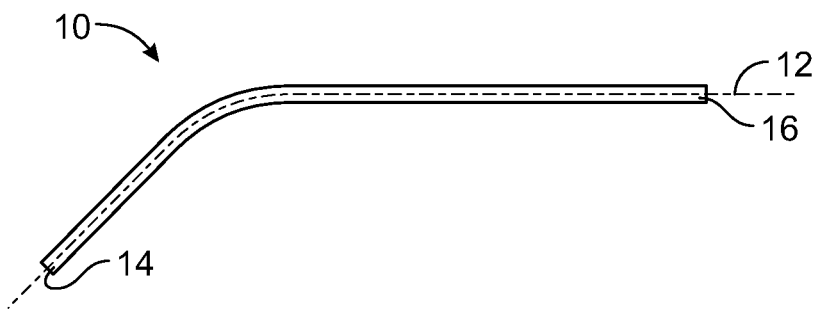
FIG. 2a is a profile view of a guide structure employed in one embodiment of the present invention.
Figure 2B:
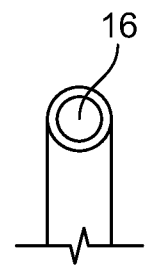

As shown in FIGS. 1a and 1b, one embodiment of a self-cleaning surgical suction device 1 comprises a suction tube 10, a guide structure 20, a bracket 30, a junction conduit 40, a tubular tip 50, a base member 60, a stylet 70, and a handle member 100; wherein, the guide structure 20 is in the form of a guide tube 20'.

In one embodiment of the self-cleaning surgical suction device 1, the suction tube 10 and guide tube 20' are substantially parallel to and coextensive with each other. As shown in FIG. 2a, the suction tube 10 includes a first longitudinal axis 12, a proximal opening 14, and a distal opening 16. In the depicted embodiment, the suction tube 10 measures about five inches to about six inches in length with an inner diameter of about five-hundredths of an inch to about a tenth of an inch and an outer diameter of about a tenth of an inch to about fifteen hundredths of an inch. Other embodiments of the present invention include a suction tube 10 that is substantially shorter or longer, having inner diameters and outer diameters that are substantially smaller or larger as befits the intended use. For example, a veterinarian about to surgically remove debris from a laceration in a large animal, appropriately sedated, would be better served using a larger surgical suction device 1; whereas, a dentist needing to sculpt a tooth in a young child would find a smaller such device more serviceable. Accordingly, the dimensions presented for the suction tube, as well as other components of the present invention, are merely examples of the various described embodiments of the present invention and are by no means to be considered limiting.

Figure 3A:
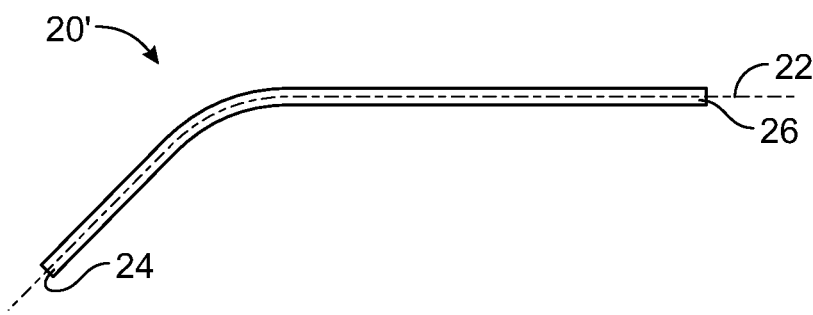
FIG. 3a is a profile view of a guide tube employed in one embodiment of the present invention.
Figure 3B:
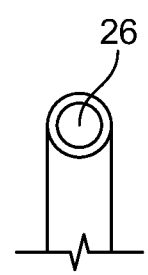

FIG. 3a illustrates the guide tube 20' which includes a second longitudinal axis 22, a proximal opening 24 and a distal opening 26. The guide tube 20' measures about five inches to about six inches in length with an inner diameter of about five-hundredths of an inch to about a tenth of an inch and an outer diameter of about a tenth of an inch to about fifteen-hundredths of an inch.

The suction tube 10 and guide tube 20' may be made from materials such as any of the following, without limitation intended: (a) metals, such as stainless steel, aluminum, and other suitable metals or alloys thereof; (b) polymers, such as polyvinylchloride, nylon, polytetrafluoroethylene, polystyrene, acrylonitrile-butadiene styrene, polypropylene, and other suitable plastics; or (c) ceramics, such as silicon carbide, tungsten carbide, apatite, and other suitable ceramics; wherein the suitable metals, alloys, plastics, or ceramics respectively have a tensile strength sufficient to maintain a tubular structure and are capable of being sterilized for medical use. One of ordinary skill in the art is necessarily familiar with the indicated range of alternative materials that have the identified characteristics associated with their suitability for the identified use.

As shown in FIG. 1, the suction tube 10 and the guide tube 20' may be bent obliquely. Alternatively, the suction tube 10 and the guide tube 20' may be bent to approximate a right angle. In yet other embodiments, the suction tube 10 and the guide tube 20' are not bent.

Figure 4:
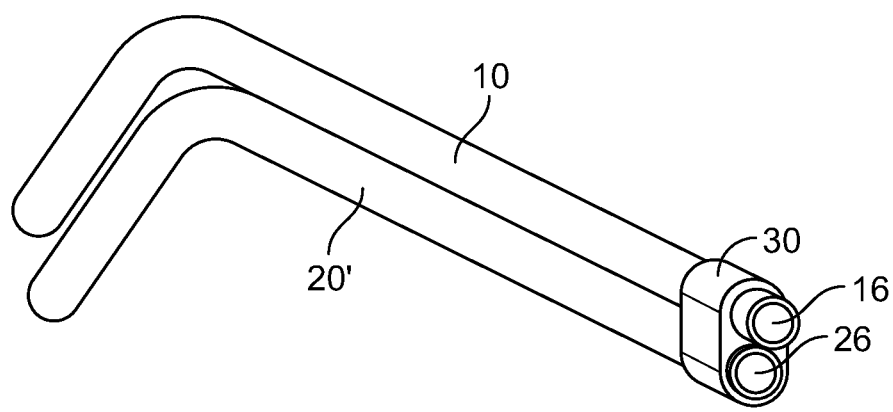
FIG. 4 is a perspective view of one embodiment wherein the distal end of the suction tube extends beyond the distal opening of the bracket.

The suction tube 10 and guide tube 20' may be conjoined by the bracket 30 proximate to the distal opening 16 of the suction tube 10 and the distal opening 26 of the guide tube 20', as illustrated by the completed assembly in FIG. 1a. The bracket 30 may be disposed at the distal end of the suction tube 10 and guide tube 20' by overmolding, frictional attachment, welding, and/or glued around the suction tube 10 and guide tube 20'. In one embodiment, the bracket is overmolded and glued around the suction tube 10 and guide tube 20'. As shown in FIG. 4, a small length of the suction tube 10 extends beyond the distal end of the bracket 30. In other embodiments a small length of both the suction tube 10 and guide tube 20' may extend beyond the distal end of the bracket 30 or a small length of the guide tube 20' may extend beyond the distal end of the bracket 30.

The distal opening 16 of suction tube 10 extending beyond the distal end of the bracket 30 is in contact with a junction conduit 40 by way of inserting the distal end of the suction tube 10 extending beyond the distal end of the bracket 30 into a proximal opening 42 of the junction conduit 40 and set by a suitable adhesive, e.g., a cyanoacrylate adhesive, such as Loctite® 4011™ or 4161™ Prism® manufactured by Henkel, such that a distal opening 44 of the junction conduit 40 is substantially coaxial with the suction tube 10 along first longitudinal axis 12, and in fluid communication with the suction tube 10.

In alternative embodiments, the distal opening 44 of the junction conduit 40 is not coaxial with the suction tube 10 along the first longitudinal axis 12. The proximal opening 42, as shown in FIG. 5b, has an elliptical shape with an inner minor axis length 43 ranging from about a tenth of an inch to about fifteen-hundredths of an inch. The junction conduit 40 may alternatively be set by welding. The junction conduit 40 may also be set by frictional attachment enabling disengagement of the junction conduit 40 from the suction tube 10.

The bracket 30 and junction conduit 40 may be made from materials such as any of the following, without limitation intended: (a) metals, such as stainless steel, aluminum, and other suitable metals or alloys thereof; (b) polymers, such as polyvinylchloride, nylon, polytetrafluoroethylene, polystyrene, acrylonitrile-butadiene styrene, polypropylene, and other suitable plastics; or (c) ceramics, such as silicon carbide, tungsten carbide, apatite, and other suitable ceramics; wherein the suitable metals, alloys, plastics, or ceramics respectively have a tensile strength sufficient to maintain the intended structure and are capable of being sterilized for medical use. One of ordinary skill in the art is necessarily familiar with the indicated range of alternative materials that have the identified characteristics associated with their suitability for the identified use.

As shown in FIG. 1, a tubular tip 50 may be in contact with the junction conduit 40. FIG. 6 illustrates that the tubular tip 50 has a proximal opening 52 and distal opening 54. The tubular tip 50 may be made of metals, alloys, polymers, or ceramics as mentioned above for alternative materials for the suction tube 10 and the guide tube 20. The proximal opening 52 and distal opening 54 have outer diameters ranging from about a tenth of an inch to about fifteen-hundredths of an inch, inner diameters ranging from about five-hundredths of an inch to about a tenth of an inch, and may or may not be uniform. In one embodiment, the tubular tip 50 is in contact with the junction conduit 40 by way of inserting the proximal end of the tubular tip 50 through the distal opening 44 of the junction conduit 40 and set by a suitable adhesive, e.g., a cyanoacrylate adhesive, such as Loctite® 4011™ or 4161™ Prism® manufactured by Henkel, such that the tubular tip 50 is coaxial with the suction tube 10 along the first longitudinal axis 12, and in fluid communication with the suction tube 10. In alternative embodiments the tubular tip 50 is not coaxial with the suction tube 10 along the first longitudinal axis 12.

The tubular tip 50 may alternatively be set by welding. The tubular tip 50 may also be fitted without welding or adhesives enabling disengagement of the tubular tip 50 from the junction conduit 40. For example, the tubular tip 50 may have an outside diameter that may allow the tip to be pushed into the distal opening 44 of the junction conduit 40 and held by frictional forces. In another example, the proximal end of the tubular tip 50 may be threaded so that it may be twisted into the junction conduit 40 which, in this example, has corresponding threads disposed proximate to the inner diameter of the distal opening 44 of the junction conduit 40.

Figure 7A:
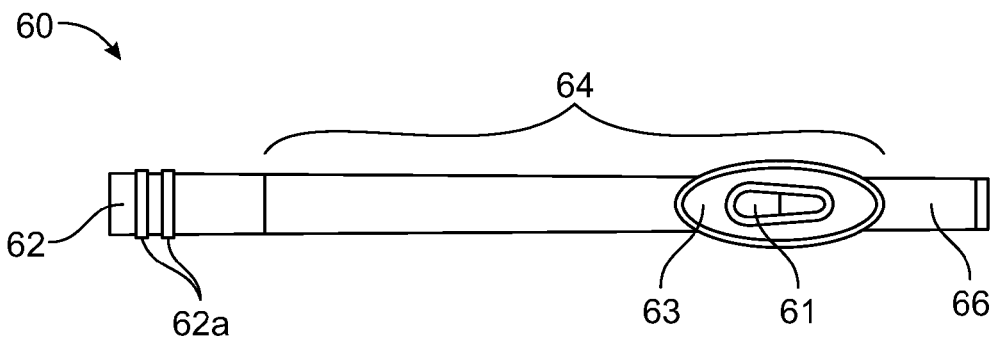
FIG. 7a is a top view of the tubular base member.

As shown in FIG. 1, an embodiment of a self-cleaning surgical suction device 1 also comprises a tubular base member 60. FIG. 7a shows that the tubular base member 60 comprises a proximal vacuum connector 62, an intermediate region 64, a distal attachment region 66, and a distal attachment opening 67 that is in fluid communication with the proximal vacuum connector 62. The tubular base 60 may be made from materials such as any of the following, without limitation intended: (a) metals, such as stainless steel, aluminum, and other suitable metals or alloys thereof; (b) polymers, such as polyvinylchloride, nylon, polytetrafluoroethylene, polystyrene, acrylonitrile-butadiene styrene, polypropylene, and other suitable plastics; or (c) ceramics, such as silicon carbide, tungsten carbide, apatite, and other suitable ceramics; wherein the suitable metals, alloys, plastics, or ceramics respectively have a tensile strength sufficient to maintain the intended structure and are capable of being sterilized for medical use. One of ordinary skill in the art is necessarily familiar with the indicated range of alternative materials that have the identified characteristics associated with their suitability for the identified use. In one embodiment, the tubular base 60 is made of acrylonitrile-butadiene styrene.

The proximal end of the suction tube 10 is inserted into the distal attachment region 66 through the distal attachment opening 67 such that the suction tube 10 is in fluid communication with the proximal vacuum connector 62. The suction tube 10 is set within the distal attachment region 66 by welding or adhesives such that the tubular base member 60 is coaxial with the suction tube 10 along the first longitudinal axis 12. In one embodiment, the suction tube 10 is set within the distal attachment region 66 by a suitable adhesive, e.g., a cyanoacrylate adhesive, such as Loctite 4011 or 4161 Prism® manufactured by Henkel. Alternative embodiments not shown include a connection such that the distal attachment region 66 is set within the suction tube 10 by welding or adhesives such that the suction tube 10 is coaxial with the tubular base member 60.

Figure 7B:
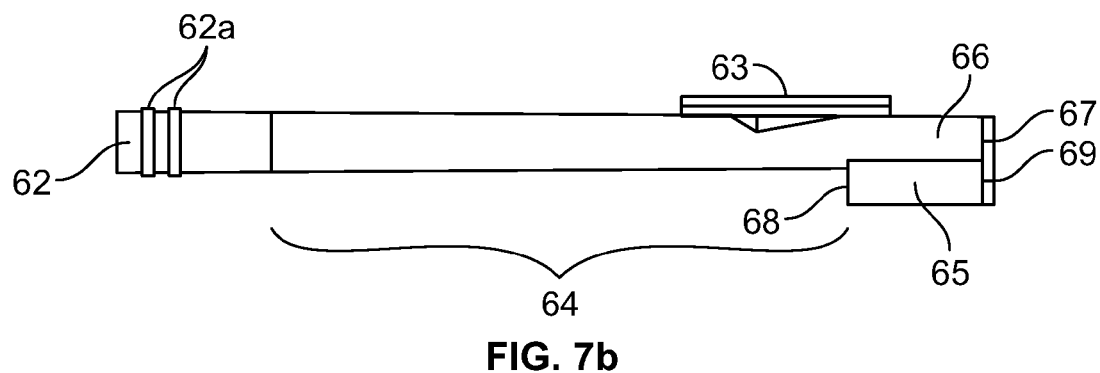
FIG. 7b is a profile view of the tubular base member.
Figure 7C:
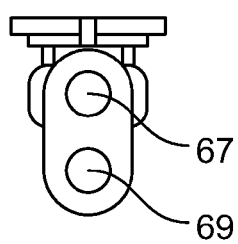
FIG. 7c is frontal view of the distal end of the tubular base member.

As shown in FIG. 7b, the tubular base member 60 also comprises a receiving member 65, a proximal receiving member opening 68, and a distal receiving member opening 69. The receiving member 65 may be disposed on the distal attachment region 66 by welding, gluing, or may be part of a monolithic mold or cast of the tubular base member 60. In one embodiment, the receiving member 65 is tubular and disposed on the distal attachment region 66 as part of a monolithic molding of the tubular base member 60 such that the receiving member 65 is substantially parallel to the distal attachment region 66.

The proximal opening 24 of the guide tube 20 is in contact with the receiving member 65 by way of inserting the proximal end of the guide tube 20 into the receiving member 65 through the distal receiving member opening 69. The guide tube 20 may be set within the receiving member 65 by welding or adhesives such that the receiving member 65 is coaxial with the guide tube 20 along the second longitudinal axis 22. In one embodiment, the guide tube 20 is set within the receiving member 65 by a suitable adhesive, e.g., a cyanoacrylate adhesive, such as Loctite 4011 or 4161 Prism® manufactured by Henkel. Alternative embodiments not shown include a connection such that the receiving member 65 is set within the guide tube 20 by welding or adhesives such that the receiving member 65 is coaxial with the guide tube 20 along the second longitudinal axis 22.

The proximal vacuum connector 62 may or may not have external threads 62a facilitating firm attachment of vacuum tubing (not shown) to the vacuum connector 62.

A vent 61, as shown in FIG. 7a, is disposed on the intermediate region 64 of the tubular base member 60 and is in fluid communication with the proximal vacuum connector 62 and the distal opening 54 of the tubular tip 50. The vent 61 can act as a muffler by decreasing the noise from rapid air flow. The vent 61 can also control the amount of negative pressure at the distal opening 54 of the tubular tip 50 by varying the amount the vent 61 is obstructed.

A vent-surrounding member 63 surrounds the vent 61 and facilitates manual control of the degree of obstruction. The vent-surrounding member 63 may be made from materials such as any of the following, without limitation intended: (a) metals, such as stainless steel, aluminum, and other suitable metals or alloys thereof; (b) polymers, such as polyvinylchloride, nylon, polytetrafluoroethylene, polystyrene, acrylonitrile-butadiene styrene, polypropylene, and other suitable plastics; or (c) ceramics, such as silicon carbide, tungsten carbide, apatite, and other suitable ceramics; wherein the suitable metals, alloys, plastics, or ceramics respectively have a tensile strength sufficient to maintain the intended structure and are capable of being sterilized for medical use. One of ordinary skill in the art is necessarily familiar with the indicated range of alternative materials that have the identified characteristics associated with their suitability for the identified use. In one embodiment, the vent-surrounding member 63 is made of acrylonitrile-butadiene styrene.

The vent surrounding member 63 may be welded to the tubular base member 60, glued to the tubular base member 60, or may be part of a monolithic mold or cast of the tubular base member 60. In one embodiment the vent surrounding member 63 is glued on the intermediate region 64 of the tubular base member 60 by a suitable adhesive, e.g., a cyanoacrylate adhesive, such as Loctite 4011 or 4161™ Prism manufactured by Henkel. In one embodiment the vent surrounding member 63 is concave and has an elliptical geometry to further aid in controlling the degree vent 61 is obstructed. Other embodiments may include a rectangular, and/or flat vent surrounding member 63. Another embodiment does not include the vent surrounding member 63.

Figure 8A:
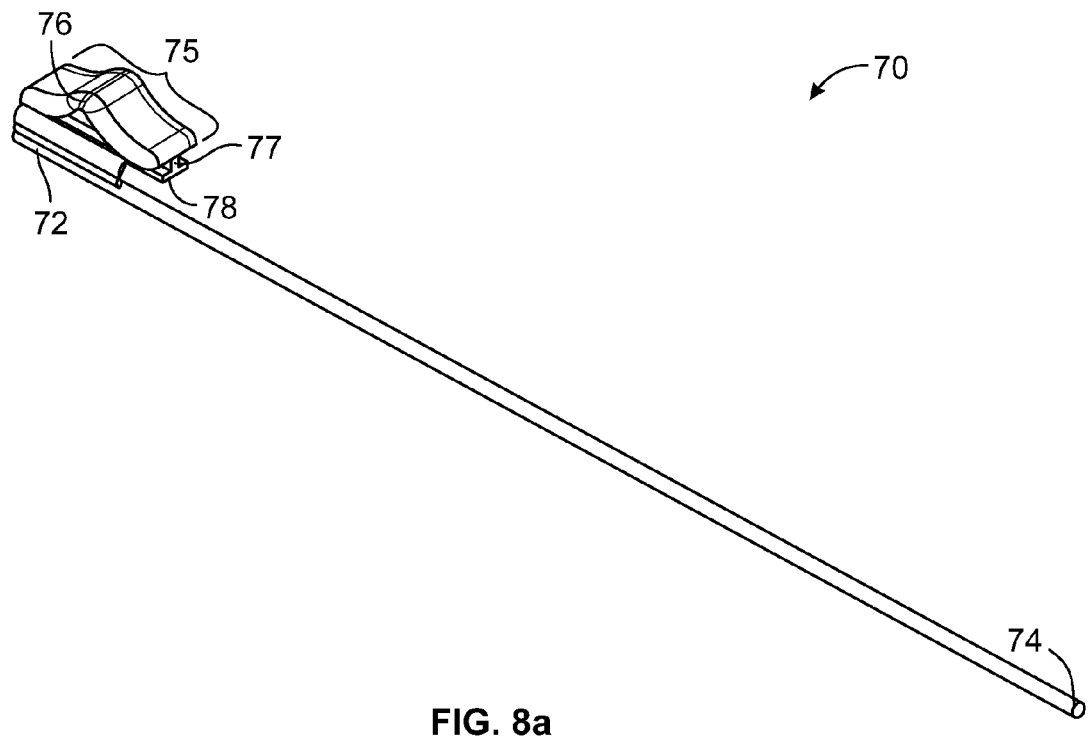
FIG. 8a is a perspective view of the stylet with the attached knob.

A stylet 70 having a proximal end 72 and distal end 74, as shown in FIG. 8a, is disposed within the guide tube 20' by inserting the distal end 74 of the stylet 70 into the proximal receiving member opening 68, through the receiving member 65, out the distal receiving member opening 69, and into the guide tube 20'. The length of stylet 70 ranges from about seven inches to about nine inches. The diameter of the stylet 70 ranges from about five-hundredths of an inch to about a tenth of an inch. The stylet 70 may be made from materials such as any of the following without limitation intended: (a) metals such as stainless steel, aluminum, and other suitable metals or alloys thereof; or (b) polymers such as nylon, polyvinylchloride, polytetrafluoroethylene, polystyrene, acrylonitrile-butadiene styrene, polypropylene, and other suitable plastics; wherein the suitable metals, alloys, or plastics respectively have the suitable elasticity for non-linear movement and can be sterilized for medical use. One of ordinary skill in the art is necessarily familiar with the indicated range of alternative materials that have the identified characteristics associated with their suitability for the identified use. In one embodiment, the stylet is composed of a polymer compound, more particularly, the stylet is composed of nylon, polyvinylchloride, polytetrafluoroethylene, polystyrene, acrylonitrile-butadiene styrene, polypropylene, and other suitable plastics, the suitability of which is a function of sufficient flexibility, stiffness, and ability to be sterilized at least once.

Figure 8B:
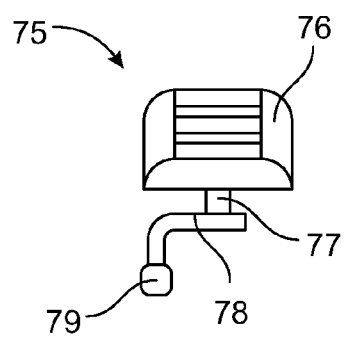
FIG. 8b is a frontal view of the knob.

As shown in FIG. 8b, a knob 75 having a node 76, a web 77, a flange 78, and a grip 79 may be fixed to the stylet 70 by welding, gluing, and/or frictionally attaching the grip 79 to about the proximal end of the stylet 70. In one embodiment the knob 75 is fixed at about the proximal end 72 of the stylet 70 by frictional attachment to the grip 79, and in another embodiment the knob 75 may be located at about the proximal end of the stylet 70 as part of a monolithic mold or cast of the stylet 70. In one embodiment, the knob 75 facilitates manual urging of the stylet 70 in the distal direction through the guide tube 20' along the second longitudinal axis 22 by manually displacing the node 76 in the distal direction. As the distal end 74 of the stylet 70 is urged through the junction conduit 40, the motion of the distal end 74 is translated from the second longitudinal axis 22 to the first longitudinal axis 12 out the distal opening 44 of the junction conduit 40 and through the tubular tip 50. The distal end 74 of the stylet 70 can be retracted by manually displacing the knob 75 by urging the node 76 towards the proximal direction. Negative pressure exhibited at the distal opening 54 of the tubular tip 50 may be varied in proportion to the manual displacement of the knob 75 as the distal end 74 of the stylet 70 coincides with the suction tube 10.

The flange 78 may take an "L" shape with a curved bend as shown from a frontal view for an embodiment of the invention shown in FIG. 8b. The flange 78 may take other shapes such as an "L" shape with a sharp angled bend or any other suitable shape that allows the flange 78 and grip 79 assembly to get around the tubular base member 60.

The knob 75 may be made from materials such as any of the following, without limitation intended: (a) metals, such as stainless steel, aluminum, and other suitable metals or alloys thereof; (b) polymers, such as polyvinylchloride, nylon, polytetrafluoroethylene, polystyrene, acrylonitrile-butadiene styrene, polypropylene, and other suitable plastics; or (c) ceramics, such as silicon carbide, tungsten carbide, apatite, and other suitable ceramics; wherein the suitable metals, alloys, plastics, or ceramics respectively have a tensile strength sufficient to maintain the intended structure and are capable of being sterilized for medical use. One of ordinary skill in the art is necessarily familiar with the indicated range of alternative materials that have the identified characteristics associated with their suitability for the identified use. In one embodiment, the knob 75 is made of acrylonitrile-butadiene styrene.

Figure 9:
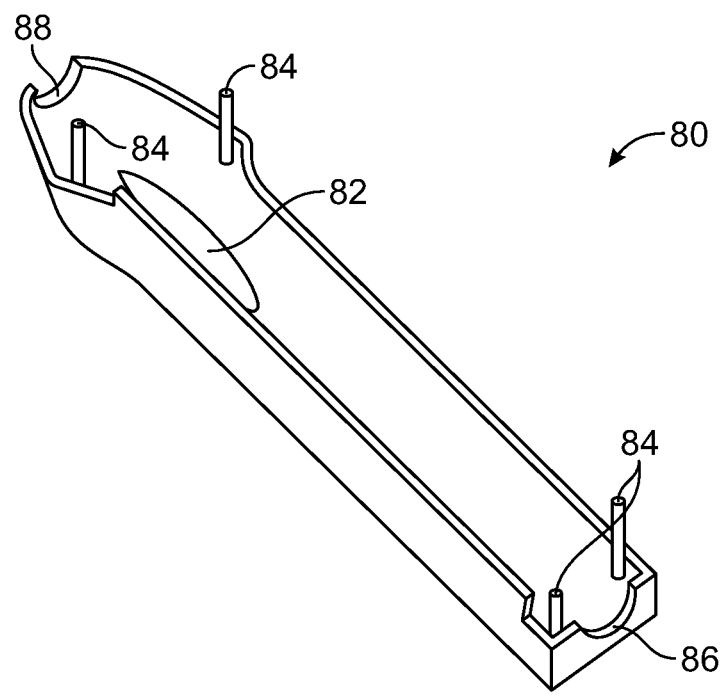
FIG. 9 is a perspective view of the dorsal handle piece.

As shown in FIG. 1, an embodiment also includes a handle member 100 comprising of a dorsal handle piece 80 and a ventral handle piece 90. The dorsal handle piece 80, as shown in FIG. 9, includes a vent-access opening 82, a plurality of interference fit posts 84, a proximal dorsal recess 86, and a distal dorsal recess 88. The dorsal handle piece 80 may be made from materials such as any of the following without limitation intended: (a) metals such as stainless steel, aluminum, and other suitable metals or alloys thereof; (b) polymers such as nylon, polyvinylchloride, polytetrafluoroethylene, polystyrene, acrylonitrile-butadiene styrene, polypropylene, and other suitable plastics; or (c) ceramics such as silicon carbide, tungsten carbide, apatite, and other suitable ceramics; wherein the material has the tensile strength to maintain the manufactured structure and can be sterilized for medical use. One of ordinary skill in the art is necessarily familiar with the indicated range of alternative materials that have the identified characteristics associated with their suitability for the identified use. In an embodiment, the dorsal handle piece 80 is made of acrylonitrile-butadiene styrene and includes four interference fit posts 84.

Figure 10:
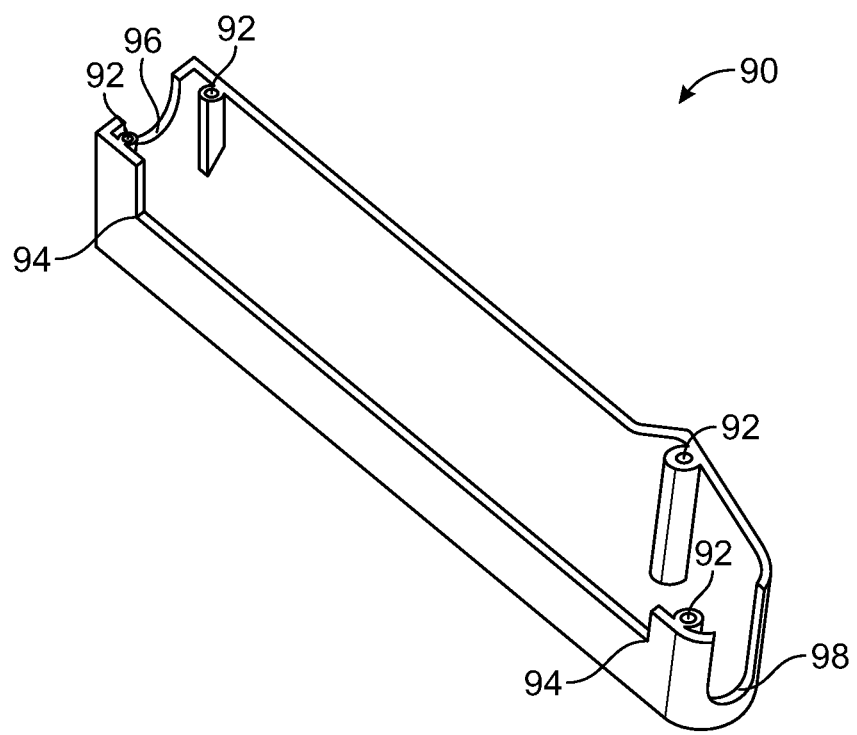
FIG. 10 is a perspective view of the ventral handle piece.

The ventral handle piece 90, as shown in FIG. 10, includes a plurality of sockets 92 that receive the interference frit posts 84 of the dorsal handle piece 80, a track element 94, a proximal ventral recess 96, and a distal ventral recess 98. The ventral handle piece 90 may be made from materials such as any of the following without limitation being intended: (a) metals such as stainless steel, aluminum, and other suitable metals or alloys thereof; (b) polymers such as nylon, polyvinylchloride, polytetrafluoroethylene, polystyrene, acrylonitrile-butadiene styrene, polypropylene, or other suitable plastics; or (c) ceramics such as silicon carbide, tungsten carbide, apatite, or other suitable ceramics; wherein the material has the tensile strength to maintain the manufactured structure and can be sterilized for medical use. One of ordinary skill in the art is necessarily familiar with the indicated range of alternative materials that have the identified characteristics associated with their suitability for the identified use. In one embodiment, the dorsal handle piece 90 is made of acrylonitrile-butadiene styrene and includes four sockets 92.

Figure 11:
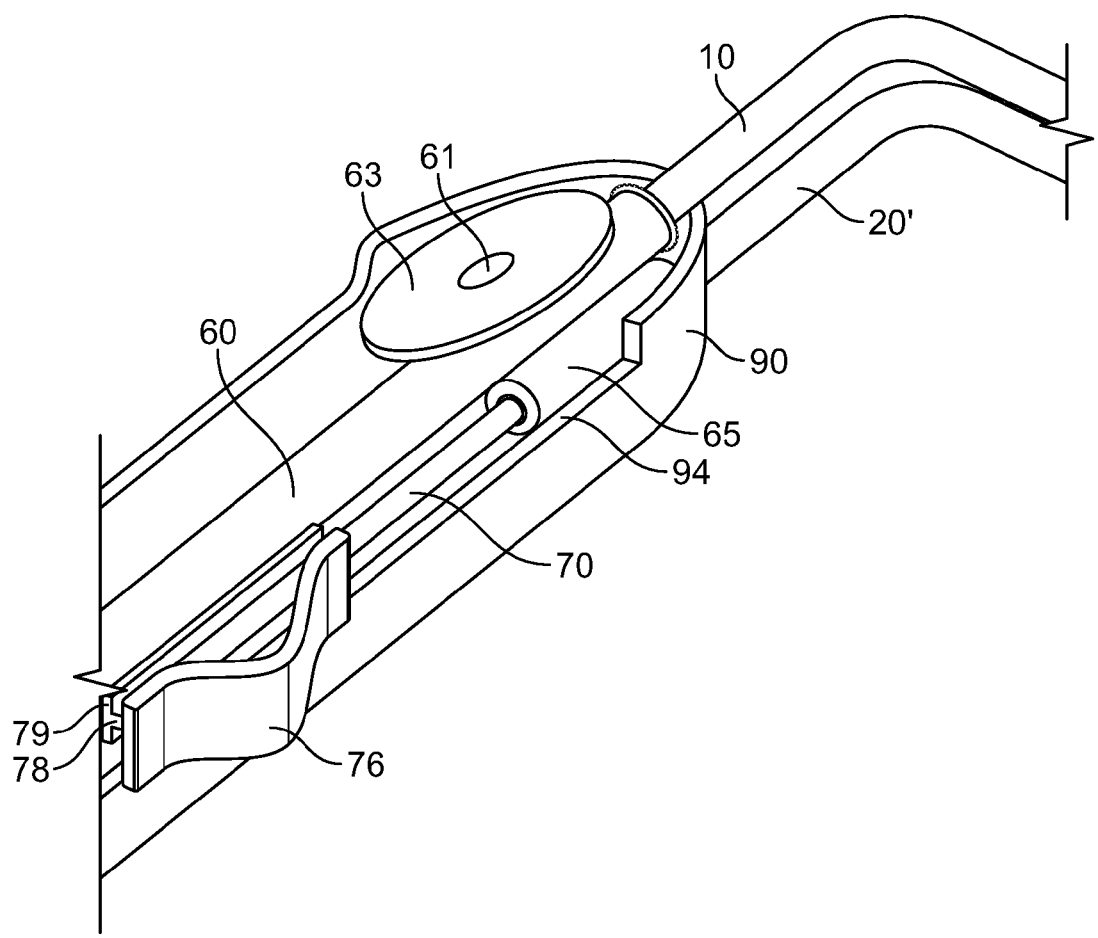
FIG. 11 is a perspective view of the tubular base, stylet, suction tube, and guide tube assembled and disposed in the ventral handle piece.

As shown in FIG. 11, the inner cavity of the ventral handle piece 90 is suitable for disposing the tubular base member 60 and the region proximate to the proximal end 72 of the stylet 70 within its inner cavity. The web 77 of the knob 75 has a proper length known to one of ordinary skill in the art to traverse the width of the track element 94 as shown in FIG. 11, thus allowing accessibility to the node 76 of the knob 75 for urging the connected stylet 70 along the second longitudinal axis 22. The plurality of interference frit posts 84 are inserted to the corresponding sockets 92 of the dorsal handle piece 80 to complete the handle member 100 surrounding the intermediate region 64 and the distal attachment region 66 of the base member 60. After inserting the interference frit posts 84 into the corresponding sockets 92, the dorsal handle piece 80 and ventral handle piece 90 may be welded, glued, and/or frictionally attached to each other. In one embodiment, the dorsal handle piece 80 is glued to the ventral handle piece 90 by a suitable adhesive, e.g., a cyanoacrylate adhesive, such as Loctite 4011 or 4161 Prism manufactured by Henkel. In other embodiments the handle member 100 may be overmolded on the tubular base member 60.

Figure 12:
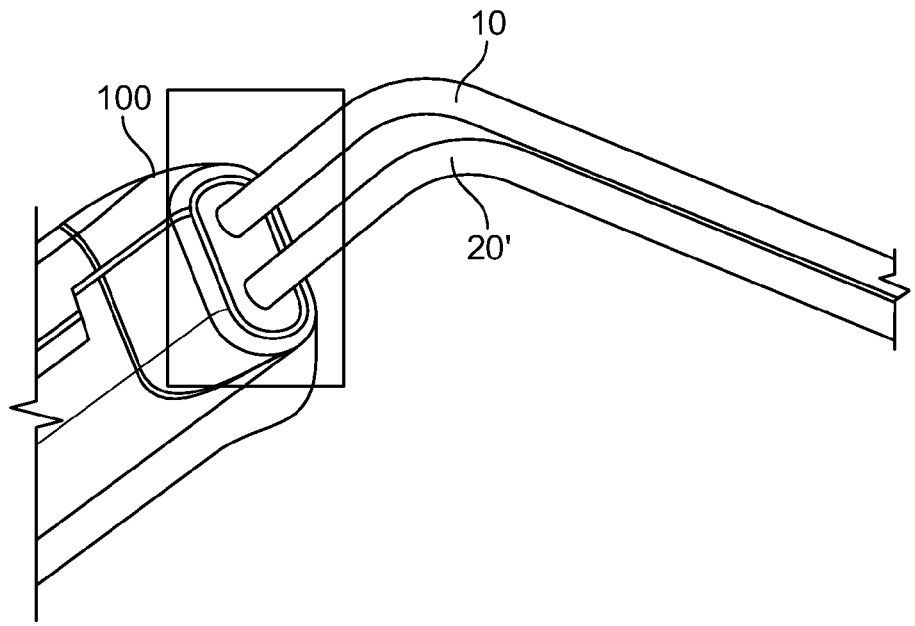
FIG. 12 is a perspective view illustrating the nearness of the distal dorsal recess and distal ventral recess to the outer wall of the distal attachment region once attachment of the handle piece is completed.

As shown in FIG. 12, the proximal dorsal recess 86 and corresponding proximal ventral recess 96 encircle the tubular base member 60 proximate to the proximal vacuum connector 62 such that the nearness of the proximal dorsal recess 86 and the proximal ventral recess 96 to the outer wall of the tubular base member 60 allows for gluing, welding, and/or frictional attachment.

The distal dorsal recess 88 and distal ventral recess 98 encircle the tubular base member 60 proximate to the distal attachment region 66 such that the nearness of the distal dorsal recess 88 and the distal ventral recess 98 to the outer wall of the tubular base member 60 allows for gluing, welding, and/or frictional attachment.

In one embodiment the dorsal hand piece 80 and the ventral hand piece 90 are glued to the outer wall of the tubular base member 60 at the proximal dorsal recess 86, the proximal ventral recess 96, the distal dorsal recess 88, and distal ventral recess 98 by a suitable adhesive, e.g., a cyanoacrylate adhesive, such as Loctite 4011 or 4161 Prism manufactured by Henkel.

The vent-access opening 82 has dimensions known to one having ordinary skill in the art to surround the vent surrounding member 61 allowing for welding, gluing, and/or frictional attachment. In one embodiment, the vent-access opening 82 is glued to the vent surrounding member 62 by a suitable adhesive, e.g., a cyanoacrylate adhesive, such as Loctite® 4011 or 4161 Prism manufactured by Henkel.

In one embodiment shown in FIG. 1, the proximal vacuum connector 62 of the tubular base member 60 remains exposed.

Figure 13:
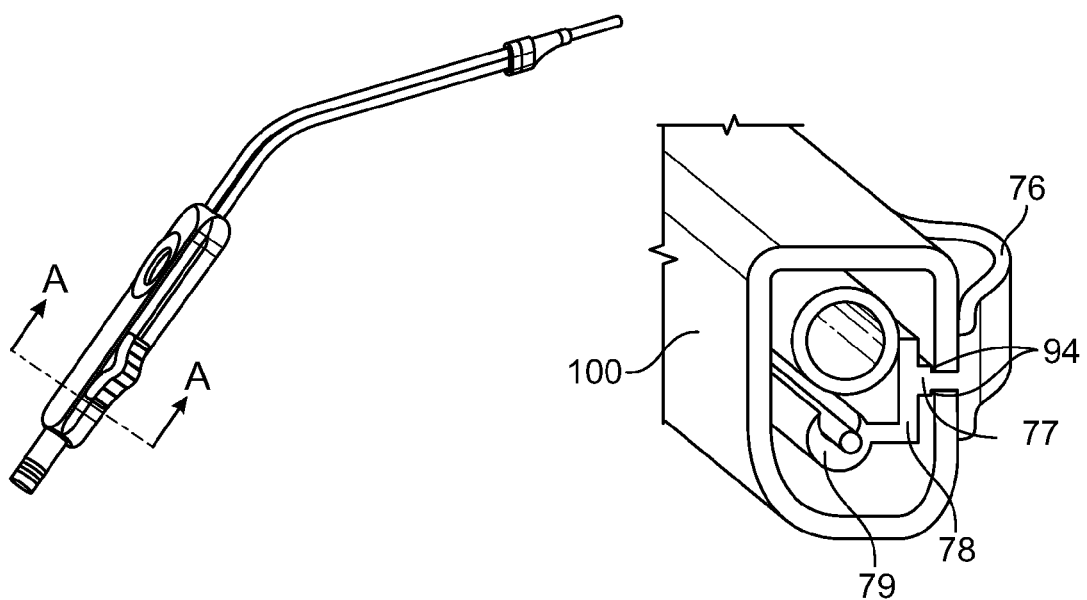
FIG. 13 is a perspective cross sectional view along section A-A of a tubular member, stylet, and knob assembled and disposed within a completed handle piece.

In one embodiment shown in FIG. 10, the depth of the track element 94 on the ventral handle piece 90 should be suitable so that by disposing the dorsal handle piece 80 on the ventral handle piece 90 limits the knob 75 to displacement that is substantially parallel to the second longitudinal axis 22 along the track element 94. In one embodiment shown in FIG. 11 and FIG. 13, the proper length of the web 77 as known to one having ordinary skill in the art restricts the flange 78 to the interior cavity of the handle member 100 which impedes lateral movement of the knob 75 and further limits the knob 75 to displacement that is substantially parallel to the second longitudinal axis 22 along the track element 94.

Figure 14:
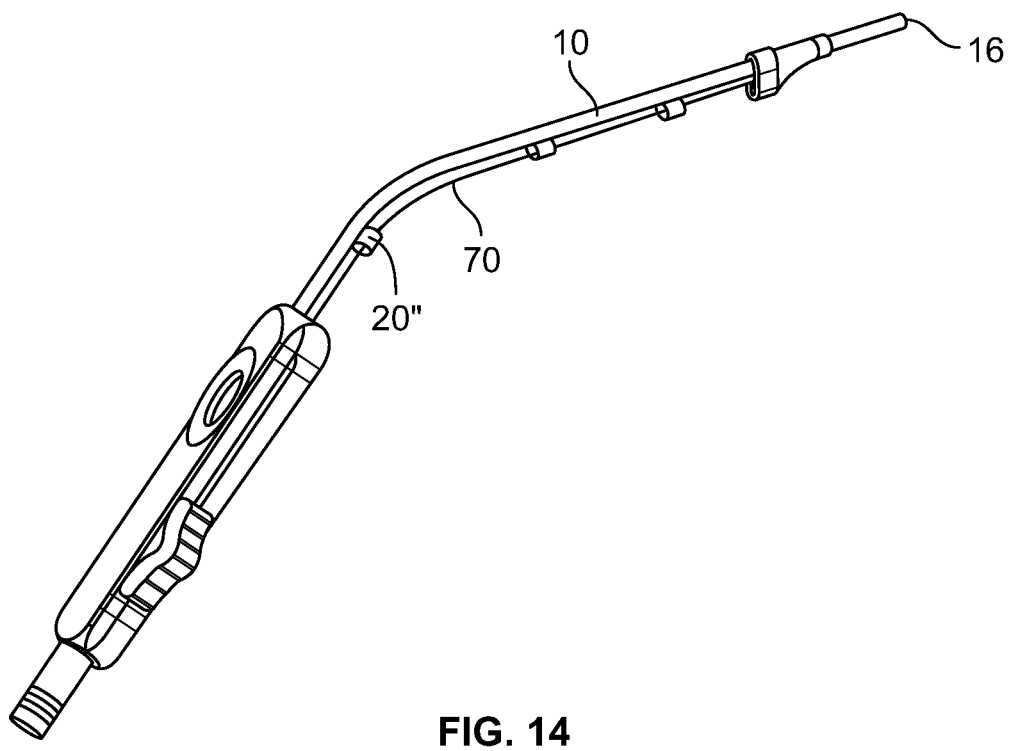
FIG. 14 is a perspective view of an alternative embodiment that utilizes at least one annulus to guide a stylet to a junction conduit.

As shown in FIG. 14, one alternative embodiment of the self-cleaning surgical suction device 1 comprises a guide structure 20 of at least one annulus 20" disposed on the suction tube 10 such that the annulus 20" guides the stylet 70 through the proximal opening 42 of the junction conduit 40 and is substantially coaxial with the second longitudinal axis 22. Furthermore, the annulus 20" should be disposed on the suction tube 10 to provide suitable guidance as the distal end 74 of the stylet 70 is urged in the distal direction substantially along the second longitudinal axis 22. The annulus 20" may be disposed on the suction tube by welding, gluing, or as part of a monolithic mold or cast of the suction tube 10. The annulus 20" may be made from materials such as any of the following without limitation intended: (a) metals such as stainless steel, aluminum, and other suitable metals or alloys thereof; (b) polymers such as nylon, polyvinylchloride, polytetrafluoroethylene, polystyrene, acrylonitrile-butadiene styrene, polypropylene, and other suitable plastics; or (c) ceramics such as silicon carbide, tungsten carbide, apatite, and other suitable ceramics; wherein the suitable metals, alloys, plastics, or ceramics respectively have a tensile strength sufficient to maintain a annular structure and are capable of being sterilized for medical use. One of ordinary skill in the art is necessarily familiar with the indicated range of alternative materials that have the identified characteristics associated with their suitability for the identified use.

Figure 15:
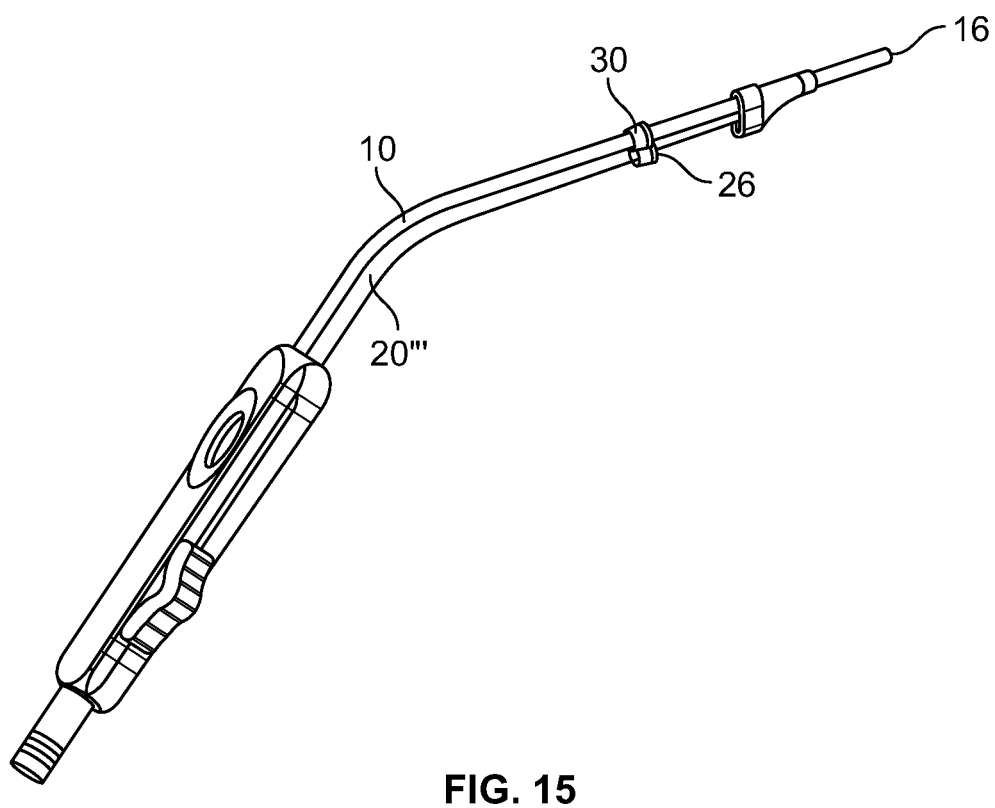
FIG. 15 is a perspective view of an alternative embodiment wherein a shortened guide tube guides a stylet into a junction conduit.

As shown in FIG. 15, one alternative embodiment of the self-cleaning surgical suction device 1 comprises a guide structure 20 in the form of a shortened guide tube 20''' having a second longitudinal axis 22, a proximal opening 24, and distal opening 26. The shortened guide tube 20''' may be made from materials such as any of the following, without limitation intended: (a) metals, such as stainless steel, aluminum, and other suitable metals or alloys thereof; (b) polymers, such as nylon, polyvinylchloride, polytetrafluoroethylene, polystyrene, acrylonitrile-butadiene styrene, polypropylene, and other suitable plastics; or (c) ceramics, such as silicon carbide, tungsten carbide, apatite, and other suitable ceramics; wherein the suitable metals, alloys, plastics, or ceramics respectively have a tensile strength sufficient to maintain a tubular structure and are capable of being sterilized for medical use. One of ordinary skill in the art is necessarily familiar with the indicated range of alternative materials that have the identified characteristics associated with their suitability for the identified use.

The shortened guide tube 20''' may be substantially parallel to the suction tube 10. The suction tube 10 and shortened guide tube 20''' may be conjoined by the bracket 30 proximate to the distal opening 16 of the suction tube 10 and the distal opening 26 of the shortened guide tube 20''', as illustrated by the completed assembly in FIG. 15. The bracket 30 may be disposed at the distal end of the suction tube 10 and shortened guide tube 20''' by overmolding, frictional attachment, welding, and/or glued around the suction tube 10 and shortened guide tube 20'''.

In the depicted embodiment of FIG. 15, the proximal opening 24 is in contact with the receiving member 65 by way of inserting the proximal end of the shortened guide tube 20''' into the receiving member 65 through the distal receiving member opening 69. The shortened guide tube 20''' may be set within the receiving member 65 by welding or adhesives such that the receiving member 65 is coaxial with the shortened guide tube 20''' along the second longitudinal axis 22. In one alternative embodiment, the shortened guide tube 20''' is set within the receiving member 65 by a suitable adhesive, e.g., a cyanoacrylate adhesive, such as Loctite 4011 or 4161 Prism manufactured by Henkel. Alternative embodiments not shown include a connection such that the receiving member 65 is set within the shortened guide tube 20''' by welding or adhesives such that the receiving member 65 is coaxial with the shortened guide tube 20''' along the second longitudinal axis 22.

Figure 16:
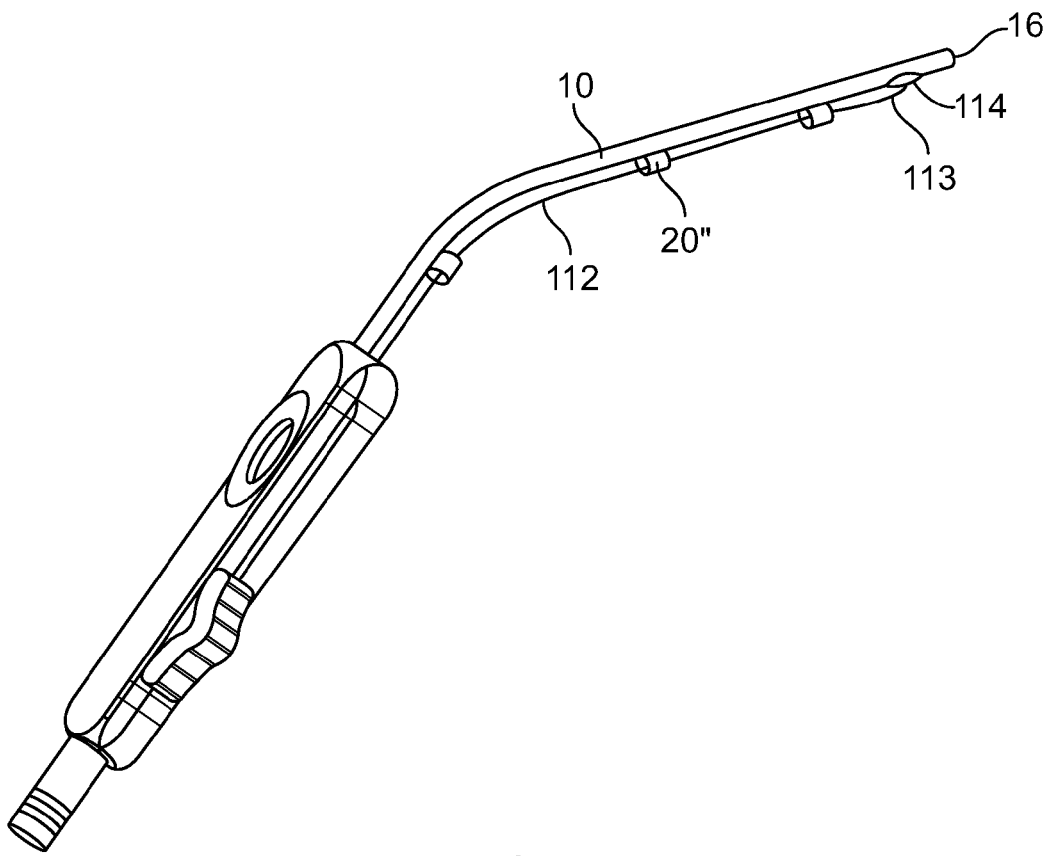
FIG. 16 is a perspective view of an alternative embodiment wherein at least one annulus is used to maintain a hooked end of a stylet in an entry port near a distal opening of a suction tube.

Another alternative embodiment of the self-cleaning surgical suction device 1, as shown in FIG. 16, does not incorporate the junction conduit 40. Instead, a hooked stylet 112 is guided by a guide structure 20 of at least one annulus 20" so that a hooked distal end 113 of the hooked stylet 112 is disposed within the entry port 114 disposed proximate to the distal end of the suction tube 10. The annulus 20" may be disposed on the suction tube by welding, gluing, or as part of a monolithic mold or cast of the suction tube 10. As the hooked stylet 112 is urged in the distal direction substantially along the second longitudinal axis 22 through the annulus 20", the curvature of the hooked distal end 113 meeting resistance from the distal edge of the entry port 114 translates the hooked stylet 112 into the suction tube 10 and to the distal opening 16 of the suction tube 10.

The hooked stylet 112 may be made from materials such as any of the following without limitation intended: (a) metals such as stainless steel, aluminum, and other suitable metals or alloys thereof, or (b) polymers such as polyvinylchloride, polytetrafluoroethylene, polystyrene, acrylonitrile-butadiene styrene, polypropylene, and other suitable plastics; wherein the suitable metals, alloys, or plastics respectively have the suitable elasticity for non-linear movement, suitable shape memory to retain a hooked disposition at the distal end of the hooked stylet 112, and can be sterilized for medical use. One of ordinary skill in the art is necessarily familiar with the indicated range of alternative materials that have the identified characteristics associated with their suitability for the identified use. The annulus 20" can be made from materials as described herein.

Figure 17:
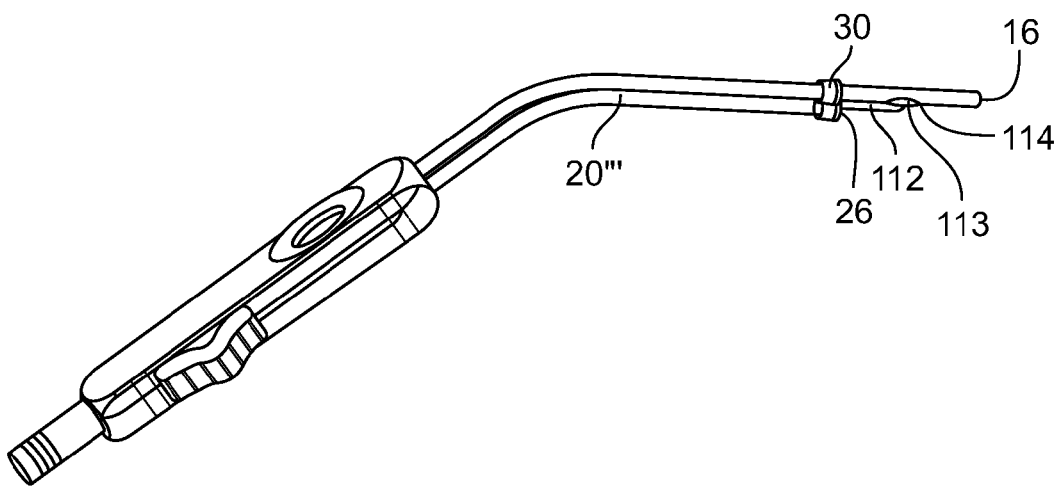
FIG. 17 is a perspective view of an alternative embodiment wherein a shortened guide tube is used to maintain a hooked end of a stylet in an entry port near a distal opening of a suction tube.

Another alternative embodiment of the self-cleaning surgical suction device 1, as shown in FIG. 17, does not incorporate the junction conduit 40. Instead, a hooked stylet 112 is guided by a guide structure 20 in the form of a shortened guide tube 20''' so that a hooked distal end 113 of the hooked stylet 112 is disposed within the entry port 114 disposed proximate to the distal end of the suction tube 10. The suction tube 10 and shortened guide tube 20''' may be conjoined by the bracket 30 proximate to the distal opening 16 of the suction tube 10 and the distal opening 26 of the shortened guide tube 20''', as illustrated by the completed assembly in FIG. 15. The bracket 30 may be disposed at the distal end of the suction tube 10 and shortened guide tube 20''' by overmolding, frictional attachment, welding, and/or glued around the suction tube 10 and shortened guide tube 20'''. As the hooked stylet 112 is urged in the distal direction substantially along the second longitudinal axis 22, the curvature of the hooked distal end 113 meeting resistance from the distal edge of the entry port 114 translates the hooked stylet 112 into the suction tube 10 and to the distal opening 16 of the suction tube 10. The hooked stylet 112 may be made from materials as described herein. The shortened guide tube 20''' can be made from materials as described herein.

Figure 18:
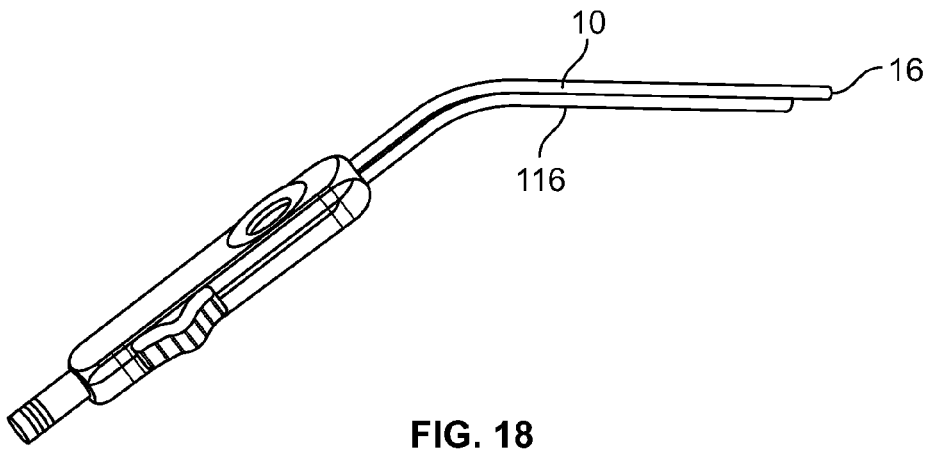
FIG. 18 is a perspective view of an alternative embodiment of the invention wherein an alternative guide tube can feed a stylet directly into a suction tube near a distal opening of a suction tube.

An alternative embodiment of the self-cleaning surgical suction device 1, as shown in FIG. 18, does not incorporate the junction conduit 40 or the tubular tip 50. Instead, the alternative embodiment of FIG. 14 comprises a guide structure 20 in the form of an alternative guide tube 116 having a longitudinal axis (not shown) which intersects the first longitudinal axis 12, a proximal opening (not shown), and a distal opening (not shown) that is in contact with an entry port 114, as shown in FIG. 16, which is disposed proximate to the distal end of the suction tube 10. The alternative guide tube 116 may be substantially parallel to the suction tube 10 until the distal opening contacts the entry port 114. Urging the stylet 70 along the longitudinal axis of the alternative guide tube 116 translates the distal end 74 of the stylet 70 through the entry port 114 of the suction tube 10 and to the distal opening 16 of the suction tube 10.

The alternative guide tube 116 may be made from materials such as any of the following without limitation intended: (a) metals such as stainless steel, aluminum, and other suitable metals or alloys thereof; (b) polymers such as polyvinylchloride, polytetrafluoroethylene, polystyrene, acrylonitrile-butadiene styrene, polypropylene, and other suitable plastics; or (c) ceramics such as silicon carbide, tungsten carbide, apatite, and other suitable ceramics; wherein the suitable metals, alloys, plastics, or ceramics respectively have a tensile strength sufficient to maintain a tubular structure and are capable of being sterilized for medical use. One of ordinary skill in the art is necessarily familiar with the indicated range of alternative materials that have the identified characteristics associated with their suitability for the identified use.

Figure 19:
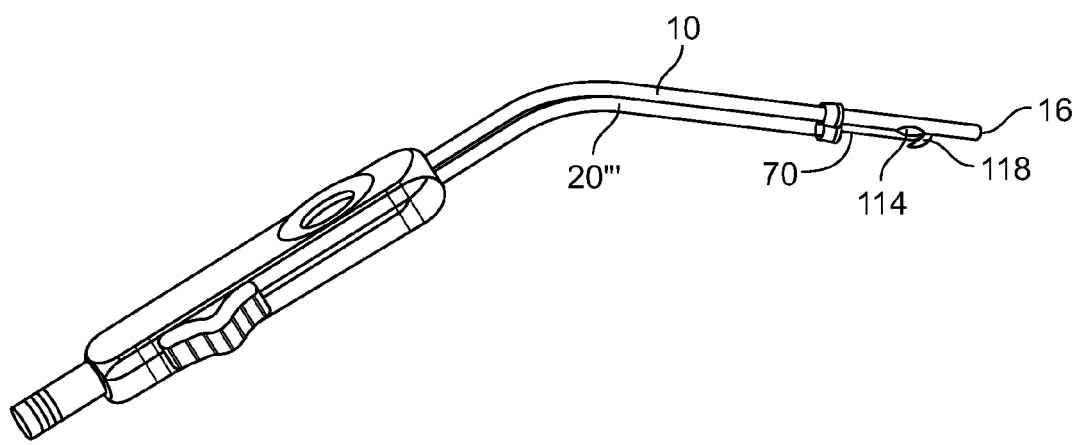
FIG. 19 is a perspective view of an alternative embodiment of the invention wherein a shortened guide tube guides a stylet to a lip.

As shown in FIG. 19, another alternative embodiment of the self-cleaning surgical suction device 1 does not incorporate the junction conduit 40 or the tubular tip 50. Instead, the alternative embodiment depicted in FIG. 19 comprises a lip 118 which functions to translate the distal movement of the stylet 70 into the entry port 114 and to the distal opening 16 of the suction tube 10. As the stylet 70 is urged through the guide structure 20 in the form of a shortened guide tube 20''', a lip 118 disposed about the distal end of the entry port 114 guides the distal end 74 along an interior slope or curvature of the lip 118 into the entry port 114 and to the distal opening 16 of the suction tube 10. The lip 118 may be disposed about the distal end of the entry port 114 as a part of the monolithic suction tube 10 structure, it may be glued about the distal end of the entry port 114, or it may be welded about the distal end of the entry port 114.

The lip 118 may be made from materials such as any of the following without limitation intended: (a) metals such as stainless steel, aluminum, and other suitable metals or alloys thereof; (b) polymers such as polyvinylchloride, polytetrafluoroethylene, polystyrene, acrylonitrile-butadiene styrene, polypropylene, and other suitable plastics; or (c) ceramics such as silicon carbide, tungsten carbide, apatite, and other suitable ceramics; wherein the suitable metals, alloys, plastics, or ceramics respectively have a tensile strength sufficient to provide suitable resistance to the translation movement of the stylet 70 such that the distal end 74 of the stylet 70 may move along the interior slope or curvature of the lip 118 structure and are capable of being sterilized for medical use. One of ordinary skill in the art is necessarily familiar with the indicated range of alternative materials that have the identified characteristics associated with their suitability for the identified use.

The suction tube 10 and shortened guide tube 20''' may be conjoined by the bracket 30 proximate to the distal opening 16 of the suction tube 10 and the distal opening 26 of the shortened guide tube 20''', as illustrated by the completed assembly in FIG. 19. The bracket 30 may be disposed at the distal end of the suction tube 10 and shortened guide tube 20''' by overmolding, frictional attachment, welding, and/or glued around the suction tube 10 and shortened guide tube 20'''.

Figure 20:
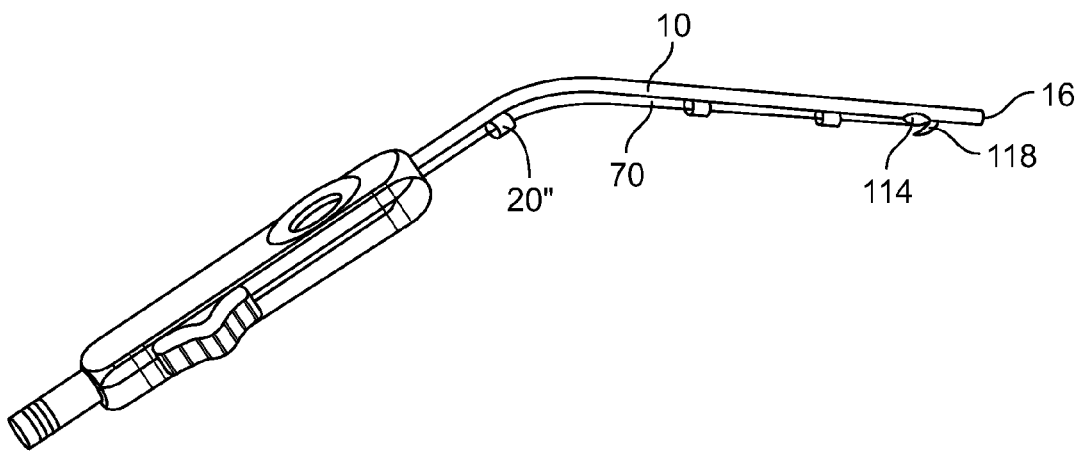
FIG. 20 is a perspective view of an alternative embodiment of the invention wherein at least one annulus guides a stylet to a lip.

Yet another alternative embodiment of the self-cleaning surgical suction device 1, as shown in FIG. 20, also does not incorporate the junction conduit 40 or the tubular tip 50. Similar to a prior embodiment shown in FIG. 19, the alternative embodiment depicted in FIG. 20 comprises a lip 118 which functions to translate the distal movement of the stylet 70 into the entry port 114 and to the distal opening 16 of the suction tube 10. However, the guide structure 20 is at least one annulus 20''. The annulus 20'' may be disposed on the suction tube by welding, gluing, or as part of a monolithic mold or cast of the suction tube 10.

As the stylet 70 is urged through at least one annulus 20'', a lip 118 disposed about the distal end of the entry port 114 guides the distal end 74 along an interior slope or curvature of the lip 118 into the entry port 114 and to the distal opening 16 of the suction tube 10. The lip 118 may be disposed about the distal end of the entry port 114 as a part of the monolithic suction tube 10 structure, it may be glued about the distal end of the entry port 114, or it may be welded about the distal end of the entry port 114. The lip 118 may be made from materials as described herein.

A common feature shared by the various embodiments described herein above is a method comprising the steps of: (a) urging a stylet 70 through a guide structure 20 along a second longitudinal axis 22; (b) translation of the stylet movement from the second longitudinal 22 axis into the suction tube 10 along a first longitudinal axis 12; and (c) retracting the stylet 70 such that the stylet 70 is disposed substantially within the guide structure 20 substantially along the second longitudinal axis 22. This method can be repeated any number of times, as required to clear obstructions from the surgical suction device of the present invention.

While the present invention has been described in its various embodiments with some degree of particularity, it is understood that this description has been provided only by way of example and that numerous changes in the details of construction, fabrication, and use, including changes in the combination and arrangement of parts or materials, may be made without departing from the spirit and scope of the invention.

What is claimed:

1. A suction device comprising:
   (a) a suction tube having a first longitudinal axis, a proximal opening, and a distal opening;
   (b) a guide structure having a second longitudinal axis that is substantially parallel to the first longitudinal axis, a proximal opening, and a distal opening;
   (c) a stylet having a proximal end and a distal end; and
   (d) a junction conduit having a proximal opening and a distal opening;
   wherein:
      the stylet is disposed along the second longitudinal axis and encircled by the guide structure, and
      the proximal opening of the junction conduit is in contact with at least the distal opening of the suction tube such that
         the distal opening of the junction conduit is in fluid communication with the suction tube, and
         urging the stylet through the guide structure along the second longitudinal axis through the junction conduit translates the distal end of the stylet to the distal opening of the junction conduit;
   (e) a tubular base member having a proximal vacuum connector, an intermediate region, a distal attachment region, and a vent disposed on the intermediate region in fluid communication with the vacuum connector that are each in fluid communication with one another, wherein the distal attachment region is in contact with the proximal opening of the suction tube such that the proximal vacuum connector is in fluid communication with the suction tube, and wherein the tubular base member further comprises a vent-surrounding member disposed on the intermediate region;
   (f) a receiving member disposed at the distal attachment region, wherein the receiving member encircles the stylet and is coaxial with the guide structure along the second longitudinal axis;
   (h) a handle member that is operably attached to and surrounds the intermediate region and distal attachment region which includes a track element extending substantially parallel to the second longitudinal axis that is proximate to the distal attachment region, and a vent-access opening such that the vent and vent-surrounding member are accessible through the vent-access opening;
   (i) a tubular tip that contacts and is in fluid communication with the junction conduit and a knob fixed at or about the proximal end of the stylet; wherein the suction tube is bent between the proximal end and distal end, the receiving member is in contact with the proximal opening of the guide structure, and the guide structure is (i) a guide tube that is substantially parallel to and coextensive with the suction tube wherein a bracket is disposed proximate to the distal end of the suction tube and proximate to the distal end of the guide tube, which bracket conjoins the suction tube and guide tube, or (ii) a shortened guide tube that is substantially parallel to the suction tube wherein a bracket is disposed proximate to the distal end of the suction tube and proximate to the distal end of the guide tube, which bracket conjoins the suction tube and guide tube, or (iii) at least one annulus disposed on the suction tube.

2. A suction device comprising:
   (a) a suction tube having a first longitudinal axis, a proximal opening, a distal opening, and an entry port disposed proximate to the distal opening;
   (b) a guide structure having a second longitudinal axis that is substantially parallel to the first longitudinal axis, a proximal opening, and a distal opening; and
   (c) a hooked stylet having a proximal end and a hooked distal end;
   wherein:
      the stylet is disposed substantially along the second longitudinal axis and encircled by the guide structure such that the hooked distal end is disposed in or proximate to the entry port, and
      as the hooked stylet is urged in the distal direction substantially along the second longitudinal axis and through the guide structure, the curvature of the hooked distal end meeting resistance from the distal edge of the entry port translates the hooked stylet into the suction tube and to the distal opening of the suction tube;
   (d) a tubular base member having a proximal vacuum connector, an intermediate region, a distal attachment region, and a vent disposed on the intermediate region in fluid communication with the vacuum connector that are each in fluid communication with one another, wherein the distal attachment region is in contact with the proximal opening of the suction tube such that the proximal vacuum connector is in fluid communication with the suction tube, and wherein the tubular base member further comprises a vent-surrounding member disposed on the intermediate region;
   (e) a receiving member disposed at the distal attachment region, wherein the receiving member encircles the stylet and is coaxial with the guide structure along the second longitudinal axis;
   (f) a handle member that is operably attached to and surrounds the intermediate region and distal attachment region which includes a track element extending substantially parallel to the second longitudinal axis that is proximate to the distal attachment region, and a vent-access opening such that the vent and vent-surrounding member are accessible through the vent-access opening;
   (g) a knob fixed at or about the proximal end of the stylet; wherein the suction tube is bent between the proximal end and distal end, the receiving member is in contact with the proximal opening of the guide structure, and the guide structure is (i) a shortened guide tube that is substantially parallel to the suction tube wherein a bracket is disposed proximate to the distal end of the suction tube and proximate to the distal end of the guide tube, which bracket conjoins the suction tube and guide tube, or (iii) at least one annulus disposed on the suction tube.

3. A suction device comprising:
   (a) a suction tube having a first longitudinal axis, a proximal opening, a distal opening, and an entry port disposed proximate to the distal opening;
   (b) a guide structure having a second longitudinal axis, a proximal opening, and a distal opening; and
   (c) a stylet having a proximal end and a distal end;
   wherein:
      the stylet is disposed substantially along the second longitudinal axis and encircled by the guide tube, and
      the distal opening of the guide structure is in contact with the entry port of the suction tube and in fluid communication with the distal opening such that urging the stylet through the guide structure substantially along the second longitudinal axis translates the distal end of the stylet through the entry port of the suction tube to the distal opening of the suction tube;
(d) a tubular base member having a proximal vacuum connector, an intermediate region, a distal attachment region, and a vent disposed on the intermediate region in fluid communication with the vacuum connector that are each in fluid communication with one another, wherein the distal attachment region is in contact with the proximal opening of the suction tube such that the proximal vacuum connector is in fluid communication with the suction tube, and wherein the tubular base member further comprises a vent-surrounding member disposed on the intermediate region;
(e) a receiving member disposed at the distal attachment region, wherein the receiving member encircles the stylet and is coaxial with the guide structure along the second longitudinal axis;
(f) a handle member that is operably attached to and surrounds the intermediate region and distal attachment region which includes a track element extending substantially parallel to the second longitudinal axis that is proximate to the distal attachment region, and a vent-access opening such that the vent and vent-surrounding member are accessible through the vent-access opening.

4. The device of claim 3, further comprising a knob fixed at or about the proximal end of the stylet; wherein the suction tube is bent between the proximal end and distal end, the receiving member is in contact with the proximal opening of the guide structure, and the guide structure is an alternative guide tube wherein the alternative guide tube is substantially parallel with the suction tube until the distal opening of the alternative guide tube connects with the entry port on the suction tube.

5. A suction device comprising:
(a) a suction tube having a first longitudinal axis, a proximal opening, a distal opening, and an entry port disposed proximate to the distal opening;
(b) a guide structure having a second longitudinal axis that is substantially parallel to the first longitudinal axis, a proximal opening, and a distal opening;
(c) a stylet having a proximal end and a distal end; and
(d) a lip disposed about the distal end of the entry port;
wherein:
the stylet is disposed along the second longitudinal axis and encircled by the guide structure, and
as the stylet is urged through the guide structure along the second longitudinal axis the distal end of the stylet moves along an interior slope or curvature of the lip and is translated through the entry port to the distal opening of the suction tube;
(e) a tubular base member having a proximal vacuum connector, an intermediate region, a distal attachment region, and a vent disposed on the intermediate region in fluid communication with the vacuum connector that are each in fluid communication with one another, wherein the distal attachment region is in contact with the proximal opening of the suction tube such that the proximal vacuum connector is in fluid communication with the suction tube, and wherein the tubular base member further comprises a vent-surrounding member disposed on the intermediate region;
(f) a receiving member disposed at the distal attachment region, wherein the receiving member encircles the stylet and is coaxial with the guide structure along the second longitudinal axis
(g) a handle member that is operably attached to and surrounds the intermediate region and distal attachment region which includes a track element extending substantially parallel to the second longitudinal axis that is proximate to the distal attachment region, and a vent-access opening such that the vent and vent-surrounding member are accessible through the vent-access opening.

6. The device of claim 5, further comprising a knob fixed at or about the proximal end of the stylet; wherein the suction tube is bent between the proximal end and distal end, the receiving member is in contact with the proximal opening of the guide structure, and the guide structure is (i) a shortened guide tube that is substantially parallel to the suction tube wherein a bracket is disposed proximate to the distal end of the suction tube and proximate to the distal end of the guide tube, which bracket conjoins the suction tube and guide tube, or (iii) at least one annulus disposed on the suction tube.

* * * * *